US006798199B2

(12) United States Patent
Larson et al.

(10) Patent No.: US 6,798,199 B2
(45) Date of Patent: Sep. 28, 2004

(54) METHOD FOR SYNCHRONIZING MAGNETIC RESONANCE IMAGING DATA TO BODY MOTION

(75) Inventors: Andrew C. Larson, Washington, DC (US); Orlando P. Simonetti, Naperville, IL (US); Richard D. White, Chagrin Falls, OH (US); Gerhard Laub, Los Angeles, CA (US)

(73) Assignees: Siemens Medical Solutions USA, Inc., Iselin, NJ (US); The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 10/360,530

(22) Filed: Feb. 6, 2003

(65) Prior Publication Data

US 2004/0155653 A1 Aug. 12, 2004

(51) Int. Cl.[7] .................................................. G01V 3/00
(52) U.S. Cl. ....................................... 324/309; 324/307
(58) Field of Search ................................. 324/309, 307, 324/306

(56) References Cited

U.S. PATENT DOCUMENTS

| | | | | | |
|---|---|---|---|---|---|
| 4,710,717 | A | * | 12/1987 | Pelc et al. | 324/309 |
| 4,728,890 | A | * | 3/1988 | Pattany et al. | 324/309 |
| 5,042,485 | A | * | 8/1991 | Sano et al. | 600/484 |
| 6,073,041 | A | * | 6/2000 | Hu et al. | 600/410 |
| 6,539,074 | B1 | * | 3/2003 | Yavuz et al. | 378/4 |
| 6,644,976 | B2 | * | 11/2003 | Kullok et al. | 434/236 |
| 2003/0225328 | A1 | | 12/2003 | DeMeester et al. | 600/419 |

OTHER PUBLICATIONS

Chia et al., "Performance of QRS Detection for Cardiac Magnetic Resonance Imaging with a Novel Vectorcardiographic Triggering Method," Journal of Magnetic Resonance Imaging, 12:678–688 (2000).

Ehman & Felmlee, "Adaptive technique for high–definition MRI of moving structures," Radiology, 173:255–263 (1988).

Fischer et al., "Novel Real–Time R–Wave Detection Algorithm Based on the Vectorcardiogram for Accurate Gated Magnetic Resonance Acquisitions," Magnetic Resonance in Medicine, 42:361–370 (1999).

Hardy et al., "Coronary Angiography by Real–Time MRI With Adaptive Averaging," Magnetic Resonance in Medicine, 44:940–946 (2000).

Kachelrieβ et al., Kymogram detection and kymogram–correlated image reconstruction from subsecond spiral computed tomography scans of the heart, Med. Phys. 29(7) (2002).

Kim et al., "Communications Cardiac Cycle Extraction from Projection Data Using Static Signal Suppression," Magnetic Resonance in Medicine, 24:182–188 (1992).

Kim et al., "Extraction of Cardiac and Respiratory Motion Cycles by Use of Projection Data and Its Application to NMR Imaging," Magnetic Resonance in Medicine, 13:25 (1990).

Lenz et al., "Retrospective Cardiac Gating: A Review of Technical Aspects and Future Directions," Magnetic Resonance Imaging, vol. 7, No. 5 (1989).

(List continued on next page.)

*Primary Examiner*—Brij B. Shrivastav
(74) *Attorney, Agent, or Firm*—Fish & Richardson P.C.

(57) ABSTRACT

Synchronizing MR images to the motion of a patient, e.g., to the beating of the heart, respiration of the lungs, or motion of a limb, by extracting timing information from the MR imaging data, itself, rather than relying solely on additional data acquired solely for timing.

40 Claims, 5 Drawing Sheets

OTHER PUBLICATIONS

Pipe, "Motion Correction With PROPELLER MRI: Application to Head Motion and Free–Breathing Cardiac Imaging," Magnetic Resonance in Medicine, 42:963–969 (1999).

Spraggins, "Wireless Retrospective Gating: Application to Cine Cardiac Imaging," Magnetic Resonance Imaging, 8:675–681 (1990).

Vasanwala et al., "Prospective MR Signal–Based Cardiac Triggering," Magnetic Resonance in Medicine, 42:82–86 (1999).

White et al., "Electrocardiograph–Independent, "Wireless" Cardiovascular Cine MR Imaging," JMRI, vol. 1, No. 3, pp. 347–355 (1991).

* cited by examiner

METHOD FOR SYNCHRONIZING MAGNETIC RESONANCE IMAGING DATA TO BODY MOTION

TECHNICAL FIELD

The invention relates to magnetic resonance (MR) imaging, and more particularly to synchronization of MR imaging data to motion of a patient.

BACKGROUND

Synchronizing MR images to the motion of a patient, e.g., to the beating of the heart, respiration of the lungs, or motion of a limb, gives the diagnostician images that have a known correspondence to the motion of interest, e.g., to the phase of the cardiac cycle. Such synchronization can be useful for both cine and still MR images. To achieve synchronization, it is necessary to have a timing signal that is indicative of the phase or position of the body. E.g., in cardiac imaging the timing signal might indicate the start of each cardiac cycle.

One technique for providing a timing signal in cardiac imaging is to connect appropriate electrodes to the patient for monitoring the patient's ECG while MR imaging data is collected. However, the magnetic fields and pulsed magnetic field gradients used in MR can interfere with the collection of the ECG signal. Special algorithms have been developed in an effort to overcome these difficulties. Chia et al., "Performance of QRS Detection for Cardiac Magnetic Resonance imaging with a Novel Vectorcardiographic Triggering Method," Journal of Magnetic Resonance Imaging, 12:678–688 (2000). Fischer et al., "Novel Real-Time R-Wave Detection Algorithm Based on the Vectorcardiogram for Accurate Gated Magnetic Resonance Acquisitions," Magnetic Resonance in Medicine, 42:361–370 (1999). Applying the ECG electrodes to the patient, and setting up to acquire the ECG data, is relatively complex and time consuming. And it can become necessary during imaging to relocate the electrodes for a viable ECG signal, and this typically requires that MR image acquisition be stopped and the patient withdrawn from the bore of the MR unit.

Synchronizing MR images is of particular value in segmented or interleaved cine imaging, in which the data for each image is derived from different cycles of the motion of interest. For the images to be meaningful, only data from corresponding phases of different cycles should be combined, hence the need to synchronize the imaging data with the motion. For example, in segmented cardiac cine imaging, the k-space lines for each image may come from 14 or more different cardiac cycles occurring during a single breath hold.

Synchronization of segmented or interleaved cine imaging can be done either prospectively or retrospectively. When done prospectively, imaging data acquisition begins in response to the timing signal derived from ECG electrodes, or alternatively from a finger pulse oximeter or other device designed to monitor a physiological signal that is synchronous with the cardiac cycle. Data acquisition typically continues for a fixed time interval, long enough to cover the systolic phase and the beginning of the diastolic phase. Then, there is typically a quiescent period until the next timing signal. Alternatively, the synchronization can be done retrospectively by continuously acquiring imaging data a synchronously with the ECG-based timing signal, while the time each line of data is acquired relative to the last trigger signal is recorded. After the acquisition, the data are assigned to the appropriate phase of the cardiac cycle based on the recorded timing data.

Attempts have been made in the prior art to derive timing information directly from MR data, in order to eliminate the need for an ECG or other additional timing measurement. But these efforts have relied on collecting additional MR data that is not used in producing the MR images.

For example, Spraggins U.S. Pat. No. 4,961,426 and Spraggins, "Wireless Retrospective Gating: Application to Cine Cardiac Imaging," Magnetic Resonance Imaging, 8:675–681 (1990) teach acquiring additional "timing slices" from which a timing signal can be derived. The timing data, in the form of an echo without phase encoding, is interleaved with imaging data acquisition (every other acquisition is timing data), and can be acquired from a different area of the heart than that being imaged (e.g., an area where motion is more visible). Kim et al., "Extraction of Cardiac and Respiratory Motion Cycles by Use of Projection Data and Its Application to NMR Imaging," Magnetic Resonance in Medicine, 13:25 (1990) uses a similar approach, except that the additional data is transformed into the spatial domain (Spraggins had used the frequency domain data directly) to provide a signal representative of a projection of an image slice onto a line oriented along the direction of time data acquisition.

Another approach is found in Vasanwala et al., "Prospective MR Signal-Based Cardiac Triggering," Magnetic Resonance in Medicine, 42:82–86 (1999), wherein a special "triggering sequence" is used to acquire velocity encoded data representative of aortic blood velocity. When a triggering event is found, the system switches from the triggering sequence to an imaging sequence.

In the area of respiratory gating, a technique known as navigator gating or navigator echo derives a timing signal from extra, non-imaging data. Ehman & Felmlee, "Adaptive technique for high-definition MRI of moving structures." Radiology, 173:255–263 (1988). Typically a projection perpendicular to the diaphragm is acquired while an edge detection algorithm is used to determine respiratory cycle position.

SUMMARY

In general, in a first aspect, the invention features synchronizing MR imaging data with motion of a patient (e.g., the beating of the heart) by extracting timing information from the MR imaging data, itself, rather than relying solely on additional data acquired solely for timing. By deriving the timing information from the MR imaging data, superior image quality is possible. For example, in cardiac imaging, where images are based on data collected during a single breath hold, more of the available time during the breath hold is available for collecting imaging data.

Superior image quality may also result from direct synchronization of the MR data with the motion affecting it, rather than some indirect measure in the form of external physiological signals, or MR signals not used in the image generation.

Clinical productivity is increased because data collection time is reduced, and because less time is required to prepare a patient for the MR study (e.g., because it is not necessary to attach ECG electrodes).

The invention solves the problem of acquiring an ECG signal in the hostile environment of an MR unit. Inability to acquire a reliable ECG signal is a common cause for failed cardiac MRI exams. Costly and complex equipment (e.g., ECG monitoring equipment) is not needed to produce the timing information.

A wide range of body motions can be synchronized, including voluntary motions like muscular contraction or chewing, as well as involuntary movements like respiration. Respiratory motion is a major cause of artifacts and poor image quality in MR scans of the chest and abdomen. Respiratory motion information can be extracted directly from the MR data and, used to synchronize the image data with the quiescent period of the respiratory cycle, avoiding motion artifacts. This allows patients with difficulty controlling their breath (e.g., elderly patients, infants) to have data collected during free breathing, avoiding the common requirement of breath holding for MRI of the chest or abdomen.

Timing signals can be derived from fetal MR data to avoid the complexity of measuring a fetal ECG, enabling the acquisition of high temporal and spatial resolution MR images of the fetal heart, something which to date has not been possible.

Preferred implementations of the first aspect of the invention may incorporate one or more of the following:

Imaging data may be acquired along radial or spiral k-space trajectories, so that timing information may be extracted from frequently collected k-space points at or near the origin. Depending on the method of extraction, the timing information may be acquired from the raw k-space data or from k-space data transformed into the spatial domain. The timing information may be based on the center point of k-space, known as the echo peak of the raw data. It may also be based on a computed 1-dimensional projection or 2-dimensional image by transforming the raw MR data into the spatial domain. More than one projection may be used to permit computation of the center of mass of the image. The projections may be onto a k-space line with an orientation chosen to enhance sensitivity to the motion of interest. Timing information may be based on correlation of low-resolution images, which may be acquired using interleaved data acquisition (e.g. with each interleaf comprising a group of k-space trajectories covering a dispersed region of k-space). The timing information may be extracted from a selected region of the low-resolution image.

The extracted timing information may be processed to provide temporal correspondence with the motion (e.g., a time value representing the time at which the motion begins or the time of another event during the motion). The processing may comprise extracting a peak, phase, or rate of a time varying signal.

The timing information may be used to retrospectively or prospectively synchronize the MR imaging data with the motion. The motion of the patient may be periodic (e.g., the periodic movement of the heart lungs). The timing information may comprise a time-varying signal that varies in value over the period of the motion. The MR imaging data may be segmented cine imaging data.

The timing information may be extracted solely from the MR imaging data or it may be extracted from a combination of MR imaging data and additional non-imaging data.

The method may be performed using an RF coil localized to the portion of the body that is moving (e.g., the RF coil may be localized over the heart).

In general, in a second aspect, the invention features a method MR imaging, comprising applying a pulse sequence that generates RF signals simultaneously on at least a first and a second RF coil; processing the RF signals acquired on the first coil to extract MR imaging data; processing the RF signals acquired on the second coil to extract data other than imaging data; and using the MR imaging data to produce an MR image.

In preferred implementations of this aspect of the invention, one or more of the following may be incporated: The invention may be applied to synchronizing MR imaging data with motion of a patient, in which case the timing data is acquired from the second RF coil, timing information indicative of the motion is extracted from the timing data, and the timing information is used to synchronize the MR imaging data with the motion. There may be a plurality of first RF coils forming an array o coils, and each is sized and positioned primarily for acquiring MR imaging data. The second RF coil may be localized to the portion of the body that is moving. The MR imaging data may comprise cardiac imaging data and the second RF coil may be localized to an area of the chest in the vicinity of the heart. The timing information may be extracted exclusively from the timing data acquired from the second RF coil. The MR imaging data may be acquired exclusively from RF signals acquired from the first RF coil.

In general, in a third aspect, the invention features synchronizing MR fetal cardiac imaging data with motion of the fetal heart by extracting timing information from MR data rather than from an ECG other non-MR signal.

In preferred implementations of this aspect of the invention, one or more of the following may be incorporated: The timing information may be extracted from MR imaging data (i.e., as with the first aspect of the invention). Alternatively, the timing information may be extracted from MR data not used as MR imaging data.

Other features and advantages of the invention will be apparent from the drawings and detailed description, and from the claims.

DETAILED DESCRIPTION

There are a great many different implementations of the invention possible, too many to possibly describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
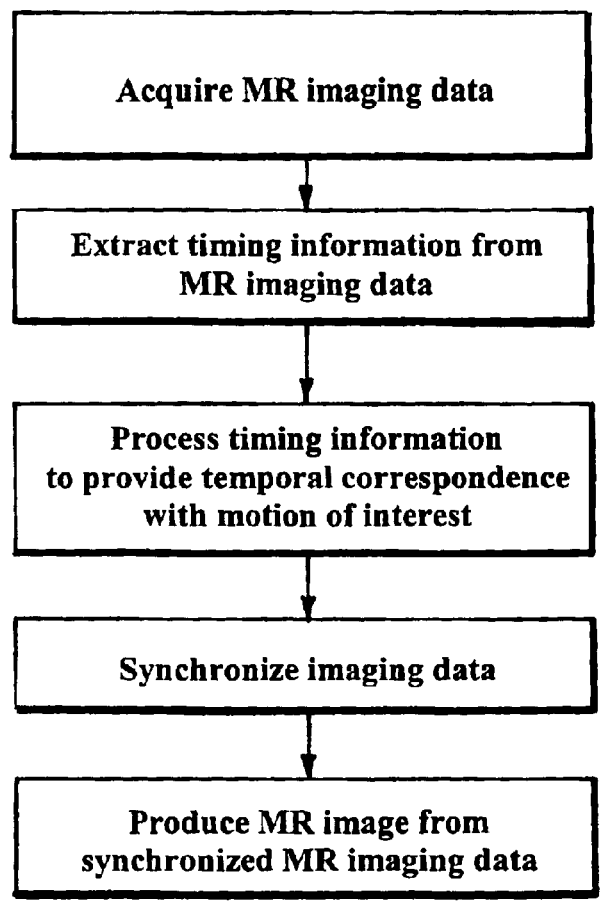
FIG. 1 is a block diagram depicting the process followed by many implementations of the invention.

FIG. 1 shows the steps common to many of these implementations. MR imaging data is acquired. Timing information is extracted from the MR imaging data. The timing information is processed to provide a temporal correspondence with the motion of interest. The imaging data is synchronized with the motion. The synchronized MR imaging data is used to produce an MR image.

MR imaging data is acquired in a manner that allows extraction of timing information reflecting motion of the patient. This is preferably done by acquiring data along k-space trajectories that frequently pass through the center (or origin) of k-space, as the value at the origin of k-space contains the echo peak, which is representative of the DC (or average) value of the spatial domain image. Having the average value of an image is usually very useful for extracting timing information as body motion tends to correlate with variation in the average value. Almost any MR image acquisition will contain some k-space trajectories that pass through the center of k space, but generally the trajectory passes through the center too infrequently to be useful for acquiring the timing signal.

Figure 2:
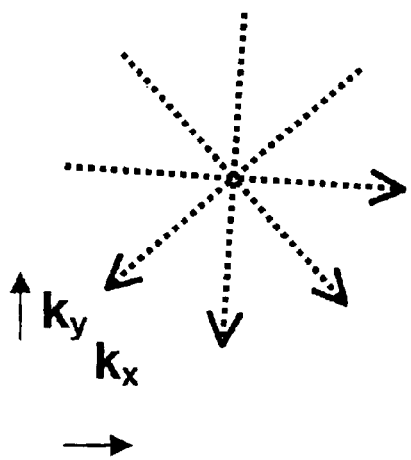
FIG. 2 is a drawing of k-space showing radial k-space acquisitions.
Figure 3:
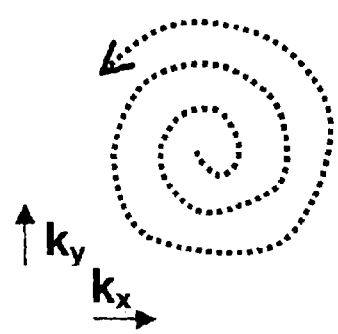
FIG. 3 is a drawing of k-space showing spiral k-space acquisitions.

There are various data acquisition strategies that can be implemented to assure that k-space origin data is frequently collected. For example, imaging data can be collected along radial or spiral k-space trajectories (FIGS. 2 and 3), as doing so inherently causes data to be frequently collected at the k-space origin 10. The concentric rectangular stripes used in so-called Propeller MRI may also be useful. Pipe, James G., "Motion Correction with PROPELLER MRI: Application to Head Motion and Free-Breathing Cardiac Imaging," Magnetic Resonance in Medicine, 42:963–969 (1999). And even Cartesian trajectories may be adapted so that data can be acquired from the central region of k-space sufficiently often to allow extraction of a useful timing signal.

It is not necessary that every data acquisition trajectory pass through the k-space origin, but it is preferred that this happen relatively frequently during data acquisition, so that extracted timing information provides temporal resolution that is high enough to represent the body motion of interest. Also, it is not absolutely necessary that it be exactly the k-space origin that the data acquisition pass through, as it may be possible for timing information to be extracted from k-space locations close to, but spaced from, the origin.

Preferably, the k-space trajectories used for acquiring imaging data are sufficient, by themselves, to provide the timing information, but in some implementations timing information is extracted primarily from k-space imaging data but also from some additional k-space data not used for imaging.

There are many possible specific techniques for extracting the timing information. For example, the timing information can be extracted from: (1) the raw k-space center point; (2) a 1-dimensional spatial domain projection; (3) multiple 1-dimensional spatial domain projections (kymogram); (4) a low-resolution, 2-dimensional image. In the first example, the timing information is acquired directly from the raw k-space data. In the others, the timing information is extracted from the transformed, spatial-domain data. Many other techniques are possible, using both raw k-space data and transformed data.

The first example simply extracts the timing information from the center point of k-space. Any k-space trajectory (e.g., radial or spiral) that frequently passes through k-space center will work with this approach.

The second and third examples process the data acquired along radial k-space trajectories to produce 1-dimensional projections of the image along those trajectories. Timing information can be extracted from a single 1-dimensional projection (second example) or from multiple projections taken from k-space lines at varying angles (third example). Computing the Fourier transform of k-space data acquired along a k-space line gives a projection of the image along a direction perpendicular to the line. Using a single projection can provide the variation of the center of mass along a selected direction, which should be chosen with consideration of the anatomy being examined. Timing information can be extracted from one such 1-dimensional projection (second example), or from several 1-dimensional projections each corresponding to a radial line along a different angle (third example). Combining projections from radial lines at different angles allows one to compute the two-dimensional center of mass of the image slice which can provide the timing information.

Figure 4:
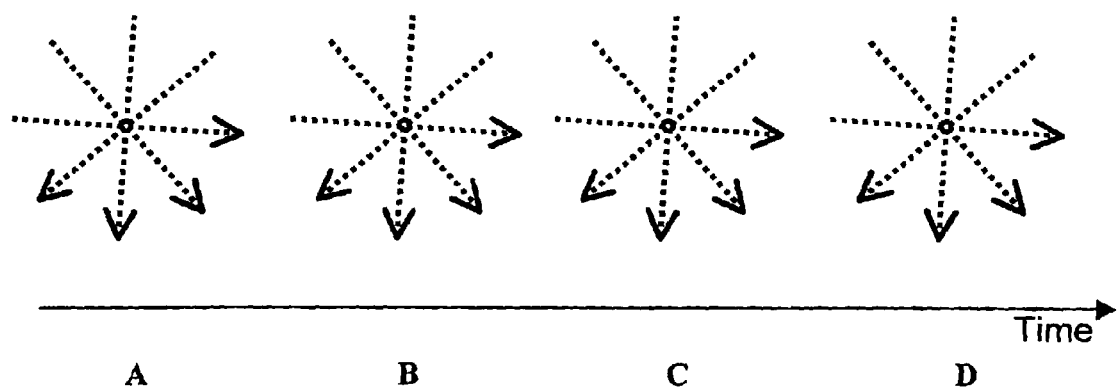
FIGS. 4 and 5 are drawings of k-space each showing a different group (interleaf) of radial k-space trajectories.
Figure 5:
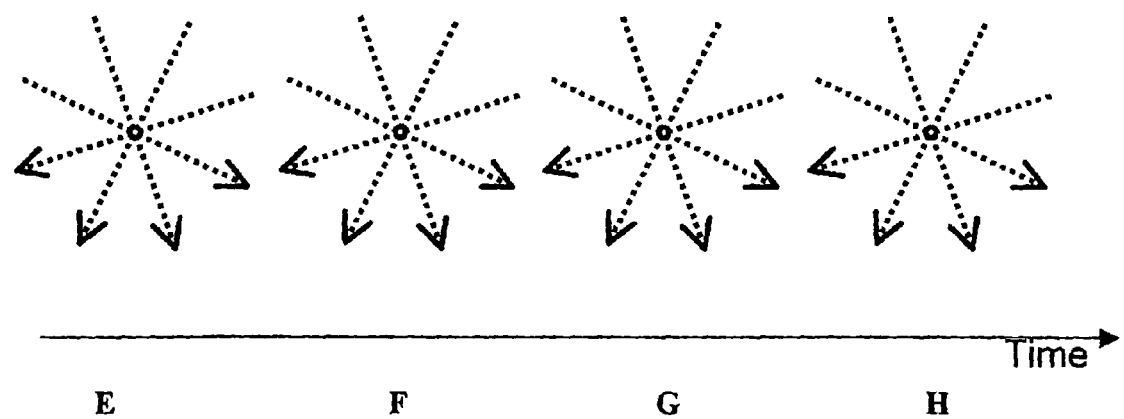

In the fourth example, data acquisition is performed with interleaved (spiral or radial) k-space trajectories that provide a series of low-resolution, 2-dimensional images, which are compared (e.g., cross-correlated) to a reference image, and the timing information is based on the result of the comparison (e.g., the time variation of computed correlation coefficients can provide the timing information). The low-resolution images may be of the entire image or of a sub-region that is likely to include the moving object of interest. FIGS. 4 and 5 are examples of interleaved radial k-space trajectories. The sets of radial trajectories, labeled A through D in FIG. 4, are acquired repeatedly for at least one complete cycle of motion, followed by the sets of radial trajectories labeled E through H in FIG. 5, which are also acquired repeatedly for at least one full cycle of motion (followed by many more interleaved sets of trajectories). A low resolution 2-dimensional image can be derived from each set of trajectories (i.e., from sets A to D in FIG. 4 and from sets E to H in FIG. 5). Alternatively, if spiral k-space trajectories are used, each spiral trajectory can, by itself, provide a low-resolution, 2-dimensional image from which timing information can be extracted.

After the timing information is extracted, the information is processed to provide a temporal correspondence with the motion of interest. Many different processing techniques can be used. The timing information may in some implementation be time-varying signal that corresponds to the motion and an algorithm may be used,to recognize in the signal a feature that corresponds to a temporal event of interest (or a particular phase of the motion of interest). But it is not essential that the timing information exist as a time-varying signal in the usual sense, as the information that is needed for synchronization may only be a single time value for each cycle of the motion being studied, and thus the algorithm may simply process the timing information to produce an output time value, without the intermediate step of there existing a time-varying signal. The result of the processing performed on the timing information may also, in some implementations, be a trigger signal that is used to initiate acquisition of imaging data.

In the case in which the timing information is a time-varying signal, various characteristics of the signal—e.g., magnitude, phase, rate of change—may be useful for synchronizing the associated imaging data. In cardiac cine imaging, the time-varying signal may be a signal representative of the blood volume that flows into and out of the slice of tissue being monitored by the MR unit. In typical short axis or long-axis orientations, periodic fluctuations result from changes in the ventricular blood pool volume. By using acquisition techniques with FLASH or TrueFISP-type sequences, the time-varying signal may have a maximum magnitude at the end of the diastolic phase of the cardiac cycle and a minimum magnitude at the end of the systolic phase. Thus, the magnitude of the signal may be directly useful for determining the time at which the heart is in a certain phase of the cardiac cycle.

Cardiac imaging also provides an example of the phase of the time-varying signal being useful. Depending on the imaging orientation, along with the gradients applied following RF excitation, the phase of the signal may correlate with the change in velocity of the circulating blood pool. This may make it possible for the phase to be used in assigning time stamps to cardiac imaging data.

The magnitude and phase of a signal have been mentioned, but in some implementations, the real or imaginary components of a signal may be directly useful for synchronizing.

Rate of change of the time-varying signal may also be of value. For example, the maximum or minimum rate of change in the signal may be useful for synchronizing the collected imaging data to a particular point in the cardiac cycle, respiratory cycle, or other involuntary or voluntary motion of the patient.

In some implementations, various signal conditioning processes may be performed on the time-varying signal to enhance its value for synchronizing the imaging data. For example, the signal may be passed through a low or band-pass filter prior to passing the signal to a peak detection algorithm to determine the maximum magnitude of the signal.

After the timing information has been processed to provide the desired temporal correspondence with the motion of interest, the imaging data is synchronized with the motion. As described above, the processing may yield a time value (e.g., of the start of a motion, or of another phase or temporal event during the motion) or it may yield a trigger signal of some kind. Synchronizing of the imaging data can be done prospectively (e.g., by using a trigger signal output to initiate acquisition of imaging data) or retrospectively (e.g., by comparing the time value of the start of a motion to time stamps associated with the imaging data).

Figure 6:
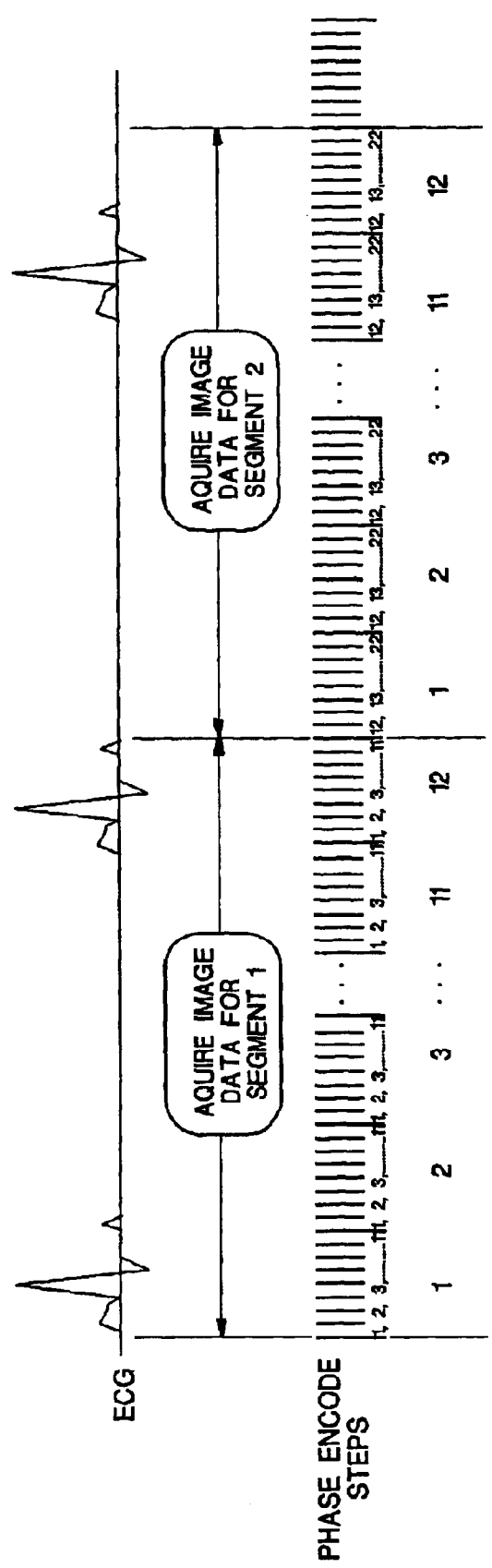
FIG. 6 is a timing diagram showing a portion of a retrospectively synchronized imaging data acquisition.

A retrospectively synchronized implementation is illustrated diagrammatically in FIG. 6. The data are acquired in a segmented fashion, so that within a given acquisition window only a portion of the k-space lines for the corresponding cine image frame are acquired. In the example shown in FIG. 6 each k-space segment is acquired 12 times during the acquisition window which is set-up to be at least as long as the longest expected cardiac cycle. Each segment has 11 k-space lines, and data is acquired over 15 acquisition windows occurring in the same breath hold (only two cycles are shown in the figure). Each image frame is made of fifteen segments of 11 k-space lines each, for a total of 165 k-space lines per image frame. Segments are continuously acquired, and timing information extracted from the imaging data is used to synchronize the acquired data retrospectively after data acquisition is complete. To synchronize the imaging data to the cardiac cycle, the time stamps of the acquired imaging data (e.g., to each acquired line) establish the time the data was acquired relative to the time the associated cardiac cycle began (that time having been derived from the timing information extracted from the imaging data).

In a prospectively-triggered implementation, the extraction and processing of timing information is done sufficiently fast enough to provide a real time, or near real time, trigger signal to affect the acquisition of imaging data. For example, in the case of cardiac segmented cine imaging, acquisition of segments of imaging data may commence when the trigger signal indicates that an R-wave has been detected. With prospective triggering, the trigger initiates the acquisition of one segment of k-space. In cine imaging, this same segment of one or more lines of data is required repeatedly until the next trigger occurs. At that point, the acquisition switches to the next segment of k-space data.

Figure 7:
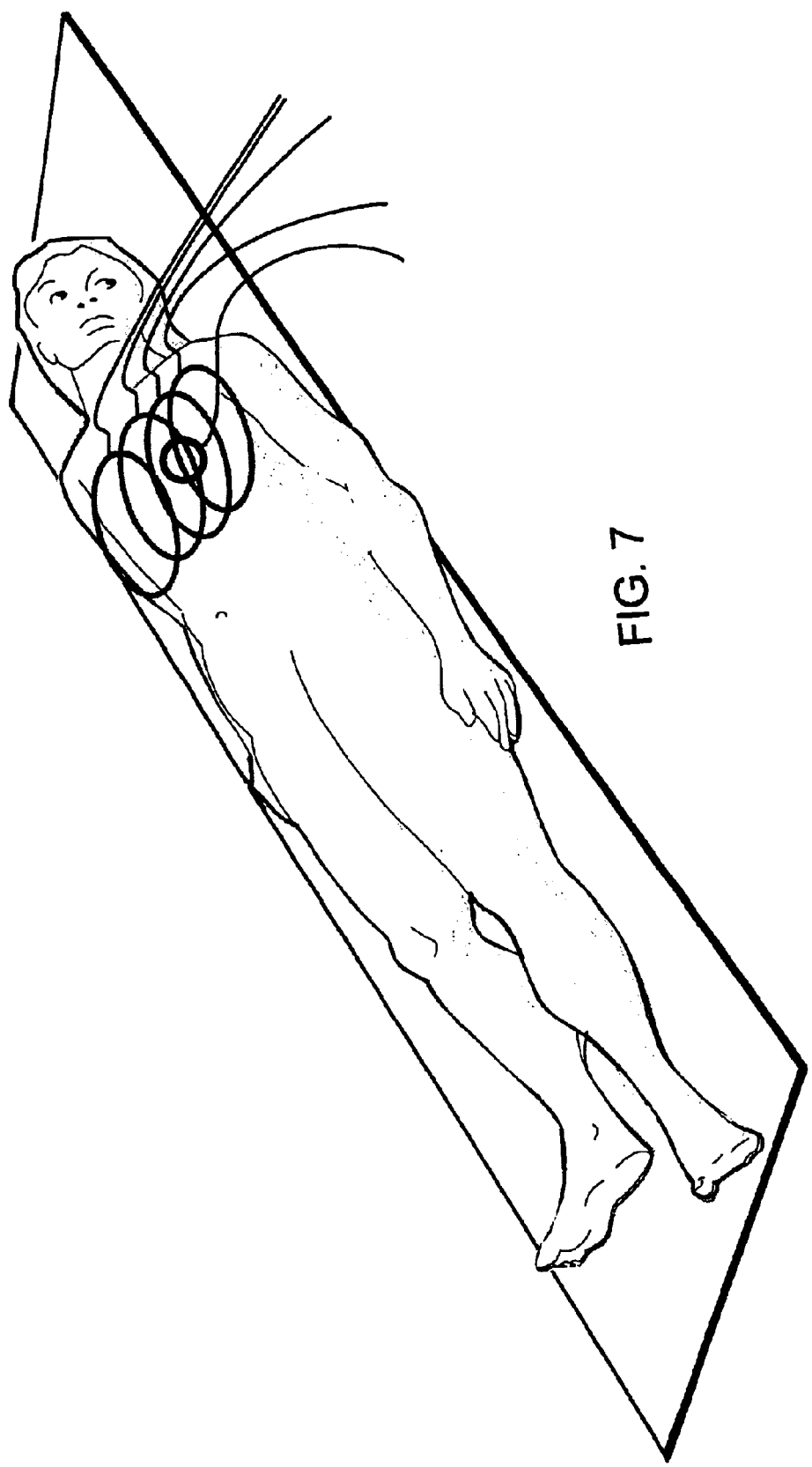
FIG. 7 is a diagrammatic view of the RF receive coils used in some implementations of the invention.
Figure 8:
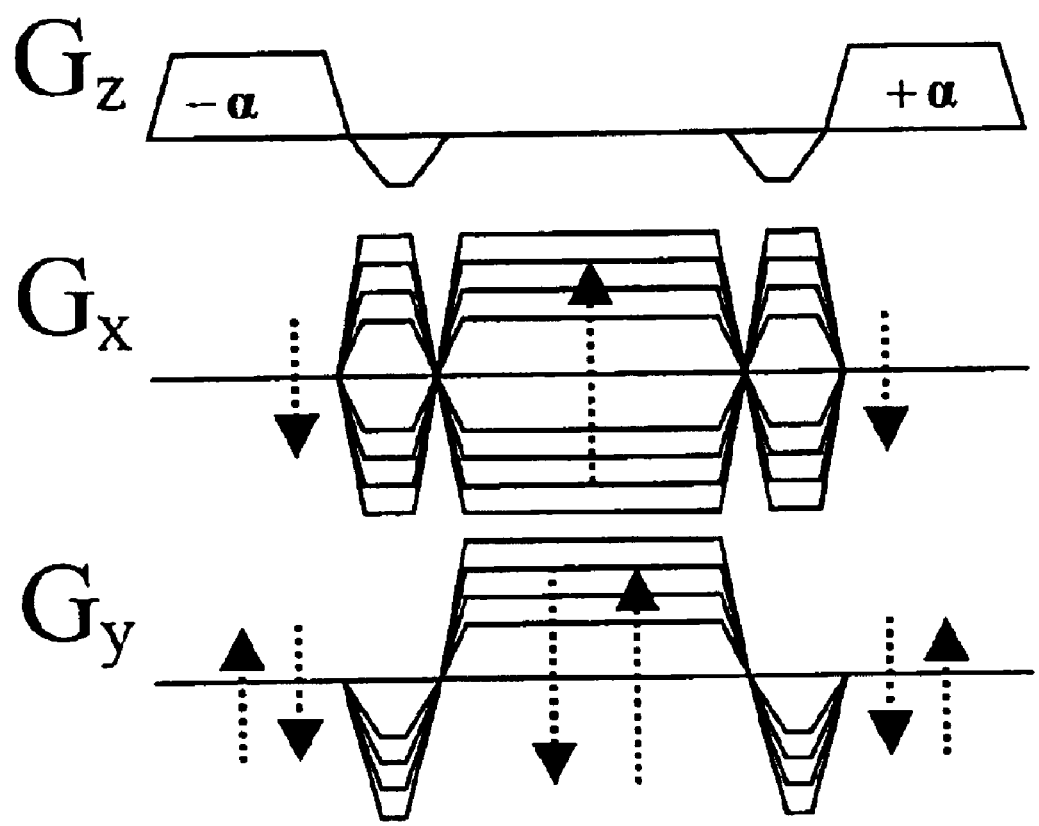
FIG. 8 shows one possible pulse sequence for providing radial k-space trajectories used in some implementations.

A conventional MR unit may be used to acquire MR imaging data, with data acquisition being along k-space trajectories as discussed above. A whole body RF transmit coil may be used to transmit the RF pulses, and a surface array of four to eight RF receive coils may be used to acquire the RF signal (FIG. 7 shows four such surface array coils). Well-known gradient coils may be used. The MR unit can use a very wide variety of pulse sequences, including the one shown in FIG. 8 (which produces radial k-spaced trajectories). Any sequence capable of providing desired k-space trajectories and acquiring imaging data quickly enough to satisfy the timing requirements will suffice. For example, for cardiac synchronization, it may be desirable to acquire timing information at least approximately every 10 milliseconds, and thus any sequence capable of acquiring data at that rate will suffice.

It is typical in MRI of the chest or abdomen to use an array of multiple independent RF (radio frequency) coil elements (as shown diagrammatically in FIG. 7) to optimize the image signal-to-noise ratio. Each of these coils contributes signal in one region of the image field-of-view, and the sensitive regions of the coils are typically overlapping each other. The signals from the multiple coils are acquired by independent receiver channels, and reconstructed independently. Combination of the information from the multiple coils typically takes place in the image domain rather than in the raw data. While all of the coils in the array may contribute useful information to the image, the variation in the image data signal related to the motion of the heart will be the strongest in a coil positioned directly over the heart. The sensitive region of this coil will be dominated by the signal from the heart, and thus be influenced the greatest by its motion. Thus, it may be advantageous to select only one of the imaging coils (with the selection done automatically based on the amplitude of the signal variation due to motion) as the source of the imaging data from which timing information is extracted.

Alternatively, it may also be advantageous to position an additional, small, local RF coil near the anatomy being imaged (e.g., on the patient's chest for cardiac imaging), and extracting timing information from the signal received by that coil. The additional coil could be smaller or larger in size than the coils used for acquiring imaging data, but there may be an advantage to making the additional coil smaller. This will tend to improve the correlation of the motion and the extracted timing information. In this case, the data from the additional coil, although resulting from the same imaging pulse sequence, and acquired essentially simultaneously with the imaging data acquired by the coil array, is not used for imaging. Such implementations are some of the possible implementations of the second aspect of the invention.

The localized RF coil—whether it is one of the coils also used for imaging or is an additional localized coil not used for imaging—serves the purpose of limiting the imaging data acquired to a small local region containing only the heart (or other moving object) thereby decreasing susceptibility to noise sources unrelated to the desired timing information.

Many other implementations of the invention other than those described above are within the invention, which is defined by the following claims. When the claims refer to "MR imaging data", they are referring to data that is used to produce MR images, and not to data that is acquired exclusively for other purposes, e.g., additional data acquired solely to provide timing information.

Features required for one aspect of the invention are not necessarily required to practice other aspects of the invention. For example, in its broadest aspects, it is not necessary to extract timing information to practice the second aspect of the invention, and in implementations when timing information is extracted it is not necessary that it be extracted from MR imaging data (e.g., it can be extracted from timing data acquired from the additional, localized coil described above). A further example is that practicing the third aspect of the invention does not require that timing information be acquired from MR imaging data.

A few examples of other implementations of the first aspect of the invention include the following:

The timing information does not need to be extracted exclusively from imaging data, as some benefit from the invention can be had by extracting the timing information primarily from imaging data but in combination with additional data taken solely for the purpose of timing.

More than one technique may be used for extracting timing information, and a choice made as to which technique is used based on the performance of the technique at achieving the desired temporal correspondence with motion, or the extracted timing information may be a weighted combination of the results of both techniques.

With selective filtering of data, both cardiac and respiratory timing information may typically be extracted from the same MR imaging data.

Implementations of the invention can be combined with other techniques for obtaining timing information. For example, respiratory motion could be synchronized with an implementation of the invention, while synchronization of cardiac imaging data is handled by conventional ECG-based timing.

What is claimed is:

1. A method of synchronizing MR imaging data with motion of a patient, the method comprising:
    acquiring MR imaging data from the patient during the motion, by acquiring imaging data for a plurality of image frames, with data being acquired for a frame from a plurality of k-space trajectories that pass through the center of k-space;
    extracting timing information from at least a portion of the MR imaging data, by acquiring timing information from a plurality of the k-space trajectories for a frame, the timing information being indicative of the motion;
    using the timing information to synchronize the MR imaging data with the motion; and
    using the synchronized MR imaging data to produce an MR image.

2. The method of claim 1 wherein the k-space trajectories comprise radial or spiral trajectories.

3. The method of claim 2 wherein the timing information is extracted from the raw k-space data.

4. The method of claim 2 wherein the timing information is extracted from k-space data transformed into the spatial domain.

5. The method of claim 3 wherein the timing information is acquired from locations at the center of k-space.

6. The method of claim 4 wherein the timing information is based on one or more computed 1-dimensional projections, each derived by transforming the raw k-space data collected along a radial k-space trajectory.

7. The method of claim 6 wherein the timing information is based on a plurality of the computed 1-dimensional projections.

8. The method of claim 7 wherein the timing information is based on a computed approximate center of mass of an image.

9. The method of claim 6 wherein the timing information is based on a computer 1-dimensional projection based on a k-space line with an orientation chosen to enhance sensitivity of the timing information to the motion.

10. The method of claim 4 wherein information is based on correlation of low-resolution images.

11. The method of claim 10 wherein the low-resolution images are acquired using interleaved data acquisition, wherein interleafs comprise groups of k-space trajectories covering a dispersed region of k-space.

12. The method of claim 1 wherein the timing information comprises a time-varying signal that varies in value over the course of the motion.

13. The method of claim 1 further comprising processing the timing information to provide temporal correspondence wit the motion.

14. The method of claim 13 wherein the processing to provide temporal correspondence provides a time value representing the time at which the motion begins or the time of another event during the motion.

15. The method of claim 13 wherein the timing information comprises a time-varying signal that varies in value over the period of the motion.

16. The method of claim 15 wherein the processing to provide temporal correspondence comprises processing the time-varying signal to extract a peak, phase, or rate of the time-varying signal.

17. The method of claim 1 wherein using the timing information to synchronize comprises using the timing information to retrospectively synchronize the MR imaging data with the motion.

18. The method of claim 1 wherein the MR imaging data is segmented cine imaging data.

19. The method of claim 1 wherein the method is performed using an RF coil localized to the portion of the body that is moving.

20. The method of claim 19 wherein the RE coil is localized over the heart.

21. The method of claim 19 wherein the RF coil is an RF receive coil and a separate RF transmit coil is used to deliver RF excitation.

22. The method of claim 1 wherein the motion of the patient is periodic.

23. The method of claim 22 wherein the motion is the periodic movement of the heart.

24. The method of claim 22 wherein the motion is the periodic movement of the lungs during respiration.

25. The method of claim 24 wherein the motion comprises both the lungs during respiration and the periodic movement of the heart, and wherein selective filtering is used so that timing information for synchronizing both motions is extracted from the same MR imaging data.

26. The method of claim 1 wherein the extracted timing information is used for synchronizing the MR imaging data with one of two motions, and the other motion is synchronized using another source of timing information.

27. The method of claim 26 wherein the motion synchronized using the extracted timing information is motion of the lungs during respiration and the other motion is the periodic movement of the heart, and the another source of timing information for synchronizing the heart is an ECG signal.

28. The method of claim 1 wherein the timing information is extracted from a combination of MR imaging data and additional non-imaging data.

29. The method of claim 28 wherein the MR imaging data is the primary source of the timing information.

30. The method of claim 1 wherein the information is extracted solely from MR inn data.

31. The method of claim 1 wherein more than one technique is used for extracting the timing information, and a choice is made as to which technique is used based on the performance of the technique at achieving the desired temporal correspondence with motion.

32. The method of claim 1 wherein more than one technique is used for extracting the timing information, and the extracted timing information is a combination of the results of both techniques.

33. A method of synchronizing MR imaging data with motion of a patient, the method comprising:

applying a pulse sequence;

acquiring RF signals simultaneously on at least a first and a second RF coil "wherein the second RF coil is dedicated to acquire timing data".

processing the RF signals acquired on the first coil to extract MR imaging data;

processing the RE signals acquired on the second coil to extract substantially only timing data; and extracting timing information from the timing data the timing information being indicative of the motion;

using the timing information to synchronize the MR imaging data with the motion;

using the MR imaging data to produce an MR image.

34. The method of claim 33 wherein the first and second RF coil are not used to transmit RF excitation during the pulse sequence.

35. The method of claim 33 wherein there are a plurality of first RF coils forming an array of coils, and each is sized and positioned primarily for acquiring MR imaging data.

36. The method of claim 33 wherein the second RF coil is localized to the portion of the body that is moving.

37. The method of claim 36 wherein the MR imaging data comprises cardiac imaging data and the second RF coil is localized to an area of the chest in the vicinity of the heart.

38. The method of claim 33 wherein the timing information is extracted exclusively from the timing data acquired from the second RF coil.

39. The method of claim 33 wherein the MR imaging data is acquired exclusively from RF signals acquired from the first RF coil.

40. The method of claim 1 wherein the method is applied to synchronizing MR fetal cardiac imaging data with motion of the fetal heart, wherein MR data is acquired from a fetus, th timing information is extracted from MR imaging data corresponding to the location of the fetal heart so that the timing information is indicative of the motion of the fetal heart; and the timing information is used to synchronize the MR imaging data with the motion of the fetal heart.

* * * * *

UNITED STATES PATENT AND TRADEMARK OFFICE
CERTIFICATE OF CORRECTION

PATENT NO. : 6,798,199 B2
DATED : September 28, 2004
INVENTOR(S) : Andrew C. Larson et al.

It is certified that error appears in the above-identified patent and that said Letters Patent is hereby corrected as shown below:

Title page,
Item [56], References Cited, U.S. PATENT DOCUMENTS, insert the following:
-- 4,961,426     10/1990         Spraggins et al. --

Column 1,
Line 30, "imaging" should be -- Imaging --.
Line 65, "a synchronously" should be -- asynchronously --.

Column 4,
Line 2, "incporated" should be -- incorporated --.
Line 9, "o" should be -- of --.

Column 6,
Line 36, after "be", insert -- a --.

Column 10,
Line 36, "RE" should be -- RF --.
Line 66, after the second occurrence of "the", insert -- timing --.
Line 67, "inn" should be -- imaging --.

Column 11,
Line 14, after the first occurrence of "coil", insert a comma.
Line 19, "RE" should be -- RF --.
Line 21, after "data", insert a comma.

Signed and Sealed this

Tenth Day of May, 2005

JON W. DUDAS
*Director of the United States Patent and Trademark Office*